United States Patent [19]
Gimet et al.

[11] Patent Number: 5,601,843
[45] Date of Patent: Feb. 11, 1997

[54] PHARMACEUTICAL TABLET COMPOSITION

[75] Inventors: Rene A. Gimet, Valbonne; Jean C. Jinot, Cagnes-sur-Mer; Christian Magnet, Chanceaux sur Choisille; Isabelle Maroteaux, Antibes, all of France; Francoise M. Nevoux, Evanston, Ill.; Roger E. Scoyer, Jemeppe-sur-Sambre, Belgium; Barbara J. Struthers, Deerfield, Ill.

[73] Assignee: G. D. Searle & Co., Chicago, Ill.

[21] Appl. No.: 276,299

[22] Filed: Jul. 18, 1994

Related U.S. Application Data

[63] Continuation of Ser. No. 973,451, Nov. 9, 1992, abandoned, which is a continuation of Ser. No. 518,353, May 3, 1990, abandoned.

[51] Int. Cl.⁶ ............................... A61K 9/30; A61K 9/28
[52] U.S. Cl. .................... 424/475; 424/464; 424/472; 424/474; 424/476; 514/573
[58] Field of Search ..................... 424/464, 472, 424/474, 475, 476, 490, 498; 514/573

[56] References Cited

U.S. PATENT DOCUMENTS

| | | | |
|---|---|---|---|
| 4,707,495 | 11/1987 | Rosenthale et al. | 514/530 |
| 4,816,472 | 3/1989 | Valcavi | 514/428 |
| 4,865,847 | 9/1989 | Gosswein | 424/439 |
| 4,954,512 | 9/1990 | Oguro et al. | 514/352 |
| 4,975,283 | 12/1990 | Patell | 424/470 |

FOREIGN PATENT DOCUMENTS

| 2135881 | 9/1984 | United Kingdom | A61K 31/557 |
|---|---|---|---|

OTHER PUBLICATIONS

IMS Market letter May 1987 vol. 14.
James et al. Arzneimittelforschung Hyperalgesia after treatment of mice with etc. 28 804–7 Jan. 1978.
Mikami et al. J. Pharm. Pharmacol. The Potentiating effects of prostaglandins on etc. 31 856–7 Jan. 1979.
Walter et al. Agents and Actions Effects of analgesics on bradykin–induced etc. 27 375–7 Jan. 1979.
Taiwo et al. J. Neurosci. Prostaglandins Inhibit Endogenous Pain Control etc. 8 1346–9 Jan. 1988.
Pateromichelakis et. Brain Research Prostaglandin E1–induced sensitization of Aa etc. 232 89–96 Jan. 1982.
Sanyal et al. Clin. Exp. Pharmacol. Physiol. Prostaglandins: antinociceptive effect of etc. 4 247–55 Jan. 1977.
Bhattacharya et al. Clin. Exp. Pharmacol. Physiol. Potentiation of antinociceptive action of etc. 2 353–357 Jan. 1975.
Ferri et al. Psychopharmacologia Decreased antinociceptive effect of morphine etc. 39 231–5 Jan. 1974.
Sanyal et al. Psychopharmacology The antinociceptive effect of etc. 60 159–63 Jan. 1979.
G. D. Searle & Co. Physician's Desk Reference Cytotec (misoprostol) Drug Information 44 2056–7 Jan. 1990.
IMS IMS Marketletter IMS Marketletter Apr. 1988.

*Primary Examiner*—Gollamudi S. Kishore
*Attorney, Agent, or Firm*—Roger A. Williams

[57] ABSTRACT

A pharmaceutical composition including a core of an NSAID selected from diclofenac and piroxicam which core is surrounded by a mantle coating of a prostaglandin, wherein an intermediate coating can be present between the NSAID core and prostaglandin mantle coating.

10 Claims, 1 Drawing Sheet

PHARMACEUTICAL TABLET COMPOSITION

This application is a continuation of application Ser. No. 07/973,451 filed Nov. 9, 1992 (now abandoned) which was a continuation of application Ser. No. 07/518,353 filed May 3, 1990 (now abandoned).

BACKGROUND OF THE INVENTION

The invention herein is directed to a pharmaceutical composition which consists of a core/mantle tablet having an inner core and an outer mantle coating surrounding the inner core. The inner core consists of an NSAID selected from diclofenac and piroxicam. The mantle coating consists of a prostaglandin such as will be described hereinafter in more detail.

Nonsteroidal anti-inflammatory drugs (NSAIDs) comprise a class of drugs which have long been recognized as having high therapeutic value especially for the treatment of inflammatory conditions such as exhibited in inflammatory diseases like osteoarthritis (OA) and rheumatoid arthritis (RA). While the NSAIDs present a beneficial therapeutic value they also exhibit undesirable side effects. An especially undesirable side effect of the administration of NSAIDs is the ulcerogenic effects generally associated with chronic use. The chronic use of NSAIDs, the use of high dosages of NSAIDs and the use of NSAIDs by the elderly can lead to NSAID induced ulcers. NSAID induced ulcers in the stomach can be dangerous. Such ulcers generally exhibit few or no symptoms and may cause dangerous bleeding when undetected. In some instances, bleeding ulcers can prove fatal. The United States Food and Drug Administration requires a class warning for all NSAIDs, which states: Serious gastrointestinal toxicity such as bleeding, ulceration, and perforation can occur at any time, with or without warning symptoms, in patients treated chronically with NSAID therapy.

Certain prostaglandins have been shown to prevent NSAID induced ulcers. Acceptable prostaglandin compounds for the invention herein and their preparation are described in U.S. Pat. Nos. 3,965,143, 4,060,691, 4,271,314 and 4,683,328. The prostaglandin compound commercially available under the USAN (United States Adopted Name) name misoprostol is a pharmaceutically acceptable prostaglandin which has been accepted for use in the treatment of NSAID induced ulcers in many countries, including the United States. Misoprostol is commercially available by prescription in such countries.

While prostaglandins are beneficial compounds and have found therapeutic usage, prostaglandins are generally considered highly unstable. Therefore, it is desirable to find prostaglandins with the desired anti-ulcerogenic properties and which can be stabilized or provided in stabilized formulations especially with respect to contemplated oral methods of delivery.

It would be desirable to provide a pharmaceutical composition which would exhibit the beneficial properties of an NSAID and which composition would exhibit the beneficial properties of a prostaglandin for countering (by inhibiting, reducing or preventing) the ulcerogenic side effects attendant to NSAID administration.

SUMMARY OF THE INVENTION

The invention herein is directed to a pharmaceutical composition comprising a core consisting of an NSAID selected from diclofenac and piroxicam and a mantle coating consisting of a prostaglandin surrounding the core. The prostaglandin preferably is an orally available prostaglandin. Acceptable prostaglandins for use herein include prostaglandins having the following structure

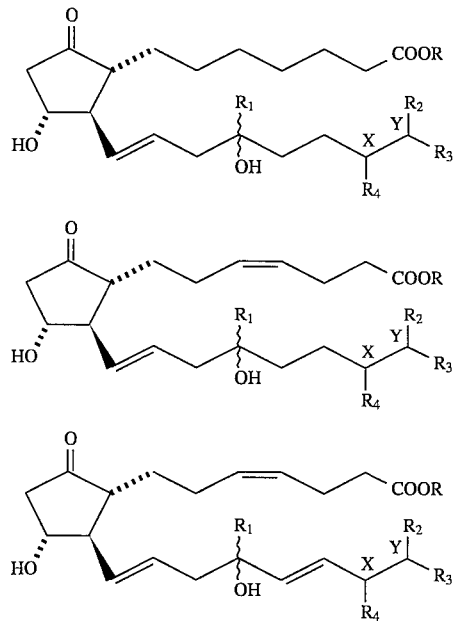

wherein R represents hydrogen or lower alkyl having 1 to 6 carbon atoms; $R_1$ represents hydrogen, vinyl or lower alkyl having 1 to 4 carbon atoms and the wavy line represents R or S stereochemistry; $R_2$, $R_3$, and $R_4$ are hydrogen or lower alkyl having 1 to 4 carbon atoms or $R_2$ and $R_3$ together with carbon Y form a cycloalkenyl having 4 to 6 carbon atoms or $R_3$ and $R_4$ together with carbons X and Y form a cycloalkenyl having 4 to 6 carbons and wherein the X-Y bond can be saturated or unsaturated.

Another embodiment of the invention herein is a pharmaceutical composition wherein a coating is provided which is an intermediate coating that surrounds the core but lies underneath the mantle coating. Such an intermediate coating can be an additional coating for preventing contact between the NSAID and the prostaglandin to thereby inhibit any deleterious or otherwise non-beneficial interaction of the NSAID and prostaglandin such as degradation of the prostaglandin. Such an intermediate coating can be an enteric coating which aids in reducing the likelihood of the NSAID dissolving in the stomach and thereby directly exposing the stomach to the NSAID.

A preferred pharmaceutical composition herein has a structure wherein the core comprises the NSAID, diclofenac in a therapeutic amount such as from 25 to 75 milligrams (mg) and a mantle coating surrounding the core comprising the prostaglandin misoprostol in a therapeutic amount of about 100 to 200 micrograms (mcg).

Another embodiment of the invention herein is a pharmaceutical composition including an NSAID core, an undercoating on the core surface of hydroxypropyl methylcellulose (HPMC), an enteric coating, an overcoat on the enteric coating of HPMC, and a mantle coating of the prostaglandin.

The invention herein will be more fully understood with regard to the following brief description of the accompanying drawings and the following detailed description.

DETAILED DESCRIPTION OF THE INVENTION

The invention herein is directed to a pharmaceutical composition which is a core/mantle tablet consisting of a core of a nonsteroidal anti-inflammatory drug (NSAID) selected from diclofenac and piroxicam. Surrounding the core is a mantle coating which consists of a prostaglandin of the structure

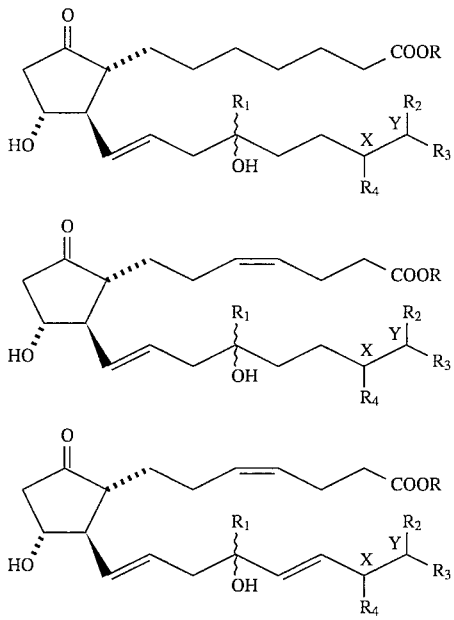

wherein R represents hydrogen or lower alkyl having 1 to 6 carbon atoms; $R_1$ represents hydrogen, vinyl or lower alkyl having 1 to 4 carbon atoms and the wavy line represents R or S stereochemistry; $R_2$, $R_3$, and $R_4$ are hydrogen or lower alkyl having 1 to 4 carbon atoms or $R_2$ and $R_3$ together with carbon Y form a cycloalkenyl having 4 to 6 carbon atoms or $R_3$ and $R_4$ together with carbons X and Y form a cycloalkenyl having 4 to 6 carbons and wherein the X-Y bond can be saturated or unsaturated.

Figure 1:
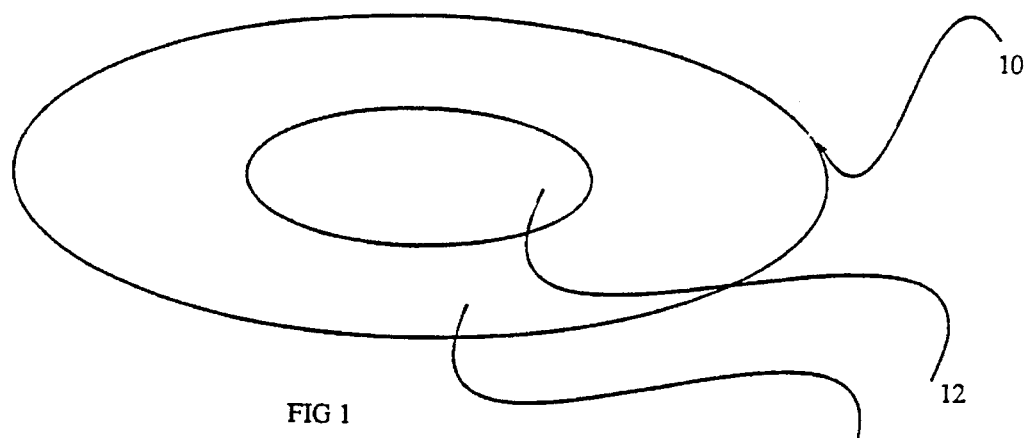
FIG. 1 is a schematic representation of a tableted pharmaceutical composition herein illustrating the core/mantle structure.
Figure 2:
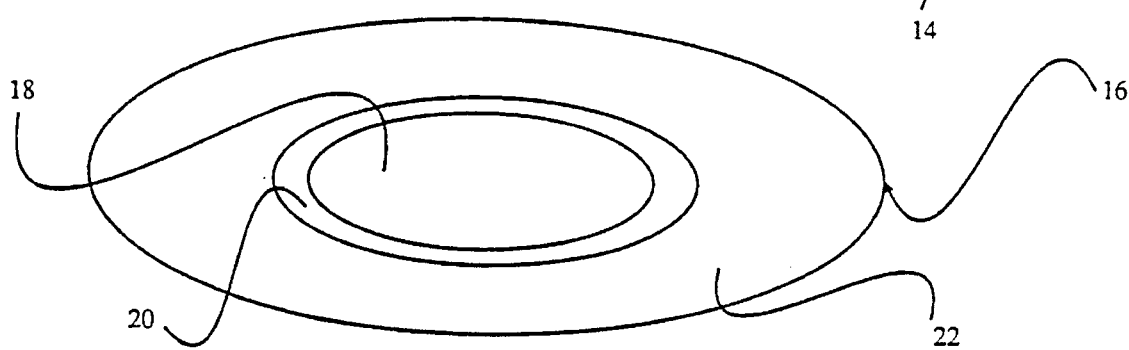
FIG. 2 is a schematic representation of another embodiment of a tableted pharmaceutical composition herein.
Figure 3:
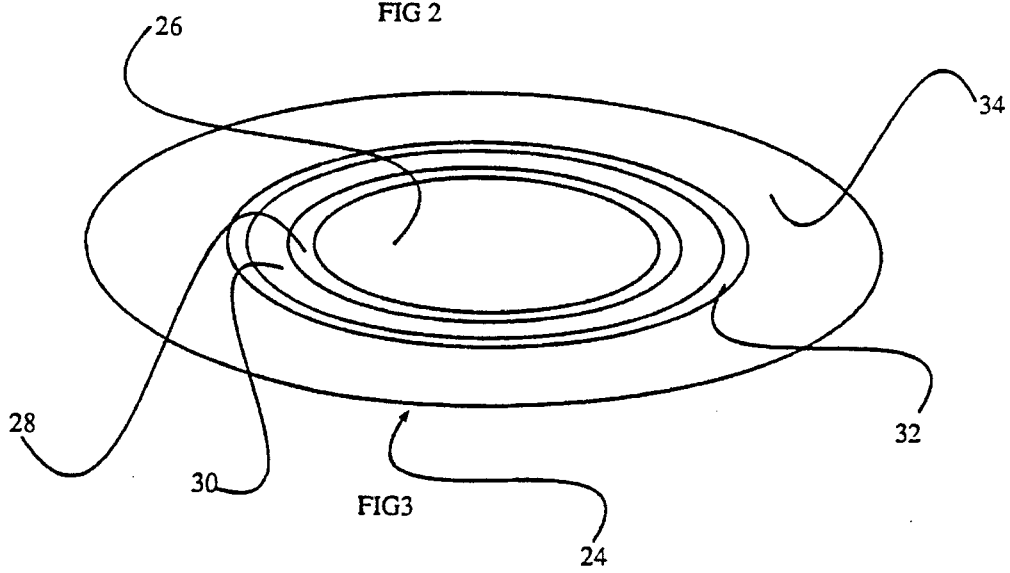
FIG. 3 is a schematic representation of still another embodiment of a tableted pharmaceutical composition herein.

The pharmaceutical composition herein can be described with regard to the accompanying drawings wherein FIGS. 1, 2 and 3 represent separate embodiments of the tableted composition herein.

The pharmaceutical composition will first be described with regard to the embodiment shown in FIG. 1. FIG. 1 represents a schematic illustration of a pharmaceutical composition herein. The pharmaceutical composition consists of a core/mantle tablet 10 which can have any geometric shape. For example, a bi-convex tablet (general pill shape) can be used which has a generally oval cross section taken along a vertical cross section and a circular cross section taken along a horizontal cross section. A bi-convex tablet can include a straight side wall (cylindrical) portion although such a tablet is not shown in the drawings herein. For ease of discussion herein a vertical cross sectional view providing an oval cross section will be used to describe the invention herein although it is understood that other shapes can be used without departing from the intended scope of the invention. A generally oval cross-section is shown in FIG. 1. The tablet 10 includes an inner core 12 which is comprised of an NSAID that is compatible with the prostaglandin as will be described in further detail hereinafter. The inner core 12 can consist of the NSAID, diclofenac or piroxicam or the pharmaceutically acceptable salts of such NSAIDs. The inner core 12 can be formulated by compressing the diclofenac or piroxicam in any suitable tableting equipment using compression tableting techniques well known in the art.

For a tablet wherein the inner core comprises diclofenac it has been found that the diclofenac can be present as diclofenac sodium. The diclofenac can be present in any therapeutically acceptable amount. For normal pharmaceutically acceptable dosing of diclofenac, diclofenac is administered in a therapeutic dosing range using tablets containing from 25 mg to 75 mg per tablet. The Physicians' Desk Reference (PDR), 44th Edition, states that the recommended dosage for treating osteoarthritis is 100 to 150 mg per day in divided doses. For treating rheumatoid arthritis the recommended dosage is 150 to 200 mg per day in divided doses. For ankylosing spondylitis the recommended dosage is 100 to 125 mg per day in divided doses. The inner core for the pharmaceutical composition herein can contain an amount from 25 to 75 mg of diclofenac and preferably a dosage of 50 mg. Various excipients such as binders, bulking agents, lubricants, fillers and the like, can be combined with the diclofenac in the core as is well known in the pharmaceutical art. Excipients used are selected from those which do not exhibit a destabilizing effect on either the diclofenac or prostaglandin.

If the inner core is piroxicam, the piroxicam can be present in a therapeutically acceptable amount. Currently, commercially available piroxicam tablets contain either 10 mg or 20 mg of piroxicam. The PDR, 44th Edition, recommends that piroxicam be administered in a single daily dose of 20 mg for rheumatoid arthritis and osteoarthritis. For the pharmaceutical composition herein the inner core can contain from 10 to 20 mg of piroxicam. Various excipients can be used in constructing a piroxicam core which excipients do not exhibit a destabilizing effect on either the piroxicam or the prostaglandin.

A mantle coating 14 surrounds the inner NSAID core and encapsulates the NSAID. The mantle coating includes a prostaglandin and more preferably an orally available prostaglandin.

The terms "prostaglandin" and/or its accepted acronym "PG" or, as more appropriately for the E-series prostaglandins, "PGE," are used herein to refer to naturally occurring or man-made E-series prostaglandins and their analogs and derivatives.

It has been found herein that acceptable prostaglandins include $E_1$ prostaglandins represented by the following Formula I:

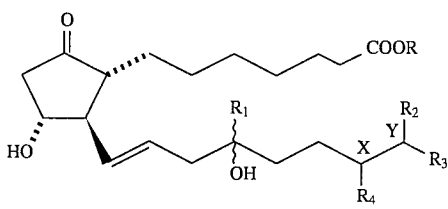

E$_2$ prostaglandins represented by the following Formula II:

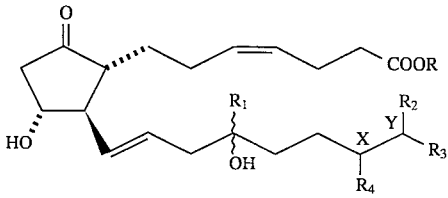

and E$_3$ prostaglandins represented by the following Formula III:

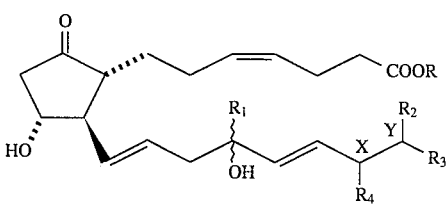

wherein R represents hydrogen or lower alkyl having 1 to 6 carbon atoms, R$_1$ represents hydrogen, vinyl or lower alkyl having 1 to 4 carbon atoms and the wavy line represents R or S stereochemistry; R$_2$, R$_3$, and R$_4$ are hydrogen or lower alkyl having 1 to 4 carbon atoms or R$_2$ and R$_3$ together with carbon Y form a cycloalkenyl having 4 to 6 carbon atoms or R$_3$ or R$_4$ together with carbons X and Y form a cycloalkenyl having 4 to 6 carbon and wherein the X-Y bond can be saturated or unsaturated.

By lower alkyl is meant straight or branched chain alkyl such as methyl, ethyl, propyl, isopropyl, butyl, secondary butyl or tertiary butyl, pentyl, or hexyl with the indicated limitation of the number of carbon atoms. The bond between carbon X and carbon Y can be saturated or unsaturated.

It has been found herein that acceptable prostaglandins include misoprostol represented by the following Formula:

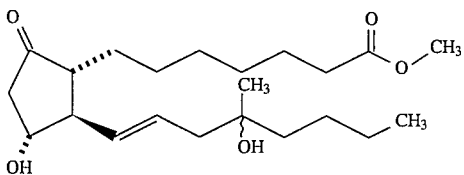

the prostaglandin enisoprost, (±)methyl 11α,16-dihydroxy-16-methyl-9-oxoprosto-4Z,13E-diene-1-oate, represented by the following Formula:

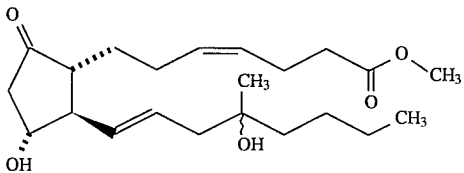

and the prostaglandin methyl 7-[2B-[6-(1-cyclopenten-1-yl)-4-hydroxy-4-methyl-1E,5E-hexadienyl]-3α-hydroxy-5-oxo-1R,1α-cyclopentyl]-4Z-heptenoate represented by the following Formula:

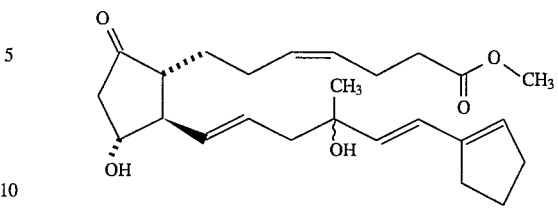

With regard to the illustrated structures, the dashed line indicates the grouping being behind the plane of the paper and the solid, blackened triangular shape indicates that the group is in front of the plane of the paper.

The prostaglandins useful in the composition of the invention herein can be prepared by known reaction schemes such as by the methods taught in U.S. Pat. Nos. 3,965,143; 4,271,314; and 4,683,328. The individual isomers can be obtained by chromatographic separation.

When the prostaglandin is misoprostol, (±)methyl 11α, 16-dihydroxy-16-methyl-9-oxoprost-13E-en-1-oate, the misoprostol is present in an amount from about 50 to about 500 mcg and preferably from about 100 to about 200 mcg.

A second embodiment of the composition is shown in FIG. 2. In FIG. 2 a tablet 16 is schematically illustrated in cross section. The tablet 16 includes an inner core 18 of an NSAID diclofenac, piroxicam or their salts such as disclosed with regard to the core 12 of FIG. 1. Surrounding the core 18 is an enteric coating 20. The enteric coating 20 can be formulated from any suitable enteric coating material, many of which are known to those skilled in the art and many of which are employed for coating commercially available NSAID's. The coating 20 aids in segregating the NSAID from the prostaglandin and in directing the dissolution of the NSAID core in the lower G.I. tract as opposed to the stomach. The coating 20 can aid in the prevention of degradation of the prostaglandin by the presence of the NSAID. The enteric coating can be coated onto the inner core using standard coating techniques. For example, aqueous or solvent coating techniques can be used to apply the enteric coating to the inner core. Surrounding the coated inner core is a mantle 22 consisting of a prostaglandin as described with regard to mantle 14 in the composition embodiment represented in FIG. 1.

A third embodiment of the composition is shown in FIG. 3. In FIG. 3 a tablet 24 is illustrated in cross section. The tablet 24 consists of an inner core 26 comprising an NSAID or its salt as disclosed with regard to the core 12 of FIG. 1. Surrounding the core 26 is an undercoat 28 which can provide a surface for the enteric coat which undercoat can have a greater affinity for the enteric coat than the core alone. The coating 28 can be any suitable coating material and preferably is HPMC in an amount about two percent (2%) by weight of the core.

An aqueous enteric coating 30 can be used to segregate the NSAID from the prostaglandin and to aid in controlling release of the NSAID. The undercoat 28 prevents water which can be present in the aqueous enteric coat 30 from penetrating into the NSAID core to cause any undesirable effects on the NSAID which might be caused by water. The enteric coating 30 can aid in the prevention of degradation of the prostaglandin by the presence of the NSAID as well as direct delivery of the NSAID in the lower G.I. tract rather than the stomach. Any aqueous enteric coating can be used and the enteric coating can be coated onto the inner core using standard coating techniques as described with regard to the embodiment shown in FIG. 2.

An overcoat 32 is coated over the enteric coat 30. The overcoat 32 can provide an intermediate coating providing affinity between the enteric coat and mantle. The overcoat can be any suitable material, preferably the overcoat is HPMC in an amount about three percent (3%) by weight of the core. The overcoat 32 prevents water which can be present in the aqueous enteric coating from passing into the prostaglandin mantle. Further, the overcoat can aid in maintaining the integrity of the enteric coating during the compression coating step as the mantle is formed on the tablet.

A mantle 34 consisting of a prostaglandin as described with regard to mantle 14 in the composition embodiment shown in FIG. 1 is coated, such as by compression coating, over the overcoat 32.

It has been found herein that an especially preferred composition is the use of misoprostol as the prostaglandin in the mantle and the use of diclofenac in the inner core.

The invention will be further described with regard to the following examples.

EXAMPLE 1

A pharmaceutical tablet composition was prepared consisting of a diclofenac sodium central core and a misoprostol mantle. The tablet had the following composition.

|  | Unit Formula (mg) |
| --- | --- |
| Core |  |
| diclofenac sodium | 50.0 |
| lactose (monohydrate) | 13.0 |
| microcrystalline cellulose | 12.9 |
| cornstarch | 8.4 |
| povidone K-30 | 4.8 |
| magnesium stearate | 0.9 |
| purified water |  |
| Mantle |  |
| misoprostol:HPMC dispersion (1:100) |  |
| misoprostol | 0.2 |
| hydroxypropyl methylcellulose (HPMC) | 20.0 |
| crospovidone | 10.0 |
| colloidal silicon dioxide | 0.5 |
| hydrogenated castor oil | 1.0 |
| micrycrystalline cellulose | 233.3 |

EXAMPLE 2

A pharmaceutical tablet composition was prepared consisting of a diclofenac sodium central core, an enteric coating and a misoprostol mantle. The tablet had the following composition.

|  | Unit Formula (mg) |
| --- | --- |
| Core |  |
| diclofenac sodium | 50.0 |
| lactose (monohydrate) | 13.0 |
| microcrystalline cellulose | 12.9 |
| cornstarch | 8.4 |
| povidone K-30 | 4.8 |
| magnesium stearate | 0.9 |
| purified water |  |
| Core coating |  |
| cellulose acetate phthalate | 5.4 |
| diethyl phthalate | 1.5 |
| Mantle |  |
| misoprostol:HPMC dispersion (1:100) |  |
| misoprostol | 0.2 |
| hydroxypropyl methylcellulose | 20.0 |
| crospovidone | 10.0 |
| collodial silicon dioxide | 0.5 |
| hydrogenated castor oil | 1.0 |
| microcrystalline cellulose | 233.3 |

EXAMPLE 3

A pharmaceutical tablet composition was prepared consisting of a diclofenac sodium central core, an aqueous enteric coating, an overcoat and a misoprostol mantle. The tablet had the following composition.

|  | Unit Formula (mg) |
| --- | --- |
| Core |  |
| diclofenac sodium | 50.0 |
| lactose (monohydrate) | 13.0 |
| microcrystalline cellulose | 12.9 |
| cornstarch | 8.4 |
| povidone K-30 | 4.8 |
| magnesium stearate | 0.9 |
| Enteric coating (aqueous) |  |
| methacrylic acid copolymer type C | 3.68 |
| sodium hydroxide | 0.049 |
| talcum | 1.84 |
| triethyl citrate | 0.37 |
| Overcoating |  |
| HPMC | 2.72 |
| polyethylene glycol (PEG 400) | 0.054 |
| Mantle |  |
| misoprostol:HPMC dispersion (1:100) |  |
| misoprostol | 0.2 |
| hydroxypropyl methylcellulose | 20.0 |
| crospovidone | 10.0 |
| colloidal silicon dioxide | 0.5 |
| hydrogentated castor oil | 1.0 |
| micrycrystalline cellulose | 233.3 |

EXAMPLE 4

A pharmaceutical tablet composition was prepared consisting of a diclofenac sodium central core, an undercoat, an enteric coating, and a misoprostol mantle. The tablet had the following composition.

|  | Unit Formula (mg) |
| --- | --- |
| Core |  |
| diclofenac sodium | 50.0 |
| lactose (monohydrate) | 13.0 |
| microcrystalline cellulose | 12.9 |
| cornstarch | 8.4 |
| povidone K-30 | 4.8 |
| magnesium stearate | 0.9 |
| Undercoat |  |
| HPMC | 1.84 |
| PEG 400 | 0.037 |
| Enteric coating (aqueous) |  |
| methacrylic acid copolymer type C | 3.68 |
| sodium hydroxide | 0.049 |

|  | Unit Formula (mg) |
|---|---|
| talcum | 1.84 |
| triethyl citrate | 0.37 |
| Mantle | |
| misoprostol:HPMC dispersion (1:100) | |
| misoprostol | 0.2 |
| hydroxypropyl methylcellulose | 20.0 |
| crospovidone | 10.0 |
| colloidal silicon dioxide | 0.5 |
| hydrogenated castor oil | 1.0 |
| microcrystalline cellulose | 233.3 |

EXAMPLE 5

A pharmaceutical tablet composition was prepared consisting of a diclofenac sodium central core, an undercoat, an enteric coating, an overcoat and a misoprostol mantle. The tablet had the following composition.

|  | Unit Formula (mg) |
|---|---|
| Core | |
| diclofenac sodium | 50.0 |
| lactose (monohydrate) | 13.0 |
| microcrystalline cellulose | 12.9 |
| cornstarch | 8.4 |
| povidone K-30 | 4.8 |
| magnesium stearate | 0.9 |
| Undercoat | |
| HPMC | 1.84 |
| PEG 400 | 0.037 |
| Enteric coating (aqueous) | |
| methacrylic acid copolymer type C | 3.68 |
| sodium hydroxide | 0.049 |
| talcum | 1.84 |
| triethyl citrate | 0.37 |
| Overcoating | |
| HPMC | 2.72 |
| PEG 400 | 0.054 |
| Mantle | |
| misoprostol:HPMC dispersion (1:100) | |
| misoprostol | 0.2 |
| hydroxypropyl methylcellulose | 20.0 |
| crospovidone | 10.0 |
| colloidal silicon dioxide | 0.5 |
| hydrogenated castor oil | 1.0 |
| microcrystalline cellulose | 233.3 |

EXAMPLE 6

A pharmaceutical tablet composition was prepared consisting of a diclofenac sodium central core, an enteric coating, an overcoat and a misoprostol mantle. The tablet had the following composition.

|  | Unit Formula (mg) |
|---|---|
| Core | |
| diclofenac sodium | 50.0 |
| lactose (monohydrate) | 13.0 |
| microcrystalline cellulose | 12.9 |
| cornstarch | 8.4 |
| povidone K-30 | 4.8 |
| magnesium stearate | 0.9 |

|  | Unit Formula (mg) |
|---|---|
| Enteric coating (aqueous) | |
| methacrylic acid copolymer type C | 3.68 |
| talcum | 1.84 |
| triethyl citrate | 0.37 |
| Overcoating | |
| HMPC | 2.72 |
| PEG 400 | 0.054 |
| Mantle | |
| misoprostol:HPMC dispersion (1:100) | |
| misoprostol | 0.2 |
| hydroxypropyl methylcellulose | 20.0 |
| crospovidone | 10.0 |
| colloidal silicon dioxide | 0.5 |
| hydrogenated castor oil | 1.0 |
| microcrystalline cellulose | 233.3 |

EXAMPLE 7

A pharmaceutical tablet composition was prepared consisting of a diclofenac sodium central core, an enteric coating, an overcoat and a misoprostol mantle. The tablet had the following composition.

|  | Unit Formula (mg) |
|---|---|
| Core | |
| diclofenac sodium | 50.0 |
| lactose (monohydrate) | 13.0 |
| microcrystalline cellulose | 12.9 |
| cornstarch | 8.4 |
| povidone K-30 | 4.8 |
| magnesium stearate | 0.9 |
| Enteric coating (aqueous) | |
| Aquateric | 6.53 |
| polysorbate 80 | 0.13 |
| diethyl phthalate (DEP) | 1.96 |
| Overcoating | |
| HMPC | 2.72 |
| PEG 400 | 0.054 |
| Mantle | |
| misoprostol:HPMC dispersion (1:100) | |
| misoprostol | 0.2 |
| hydroxypropyl methylcellulose | 20.0 |
| crospovidone | 10.0 |
| colloidal silicon dioxide | 0.5 |
| hydrogenated castor oil | 1.0 |
| microcrystalline cellulose | 233.3 |

EXAMPLE 8

A pharmaceutical tablet composition was prepared consisting of a diclofenac sodium central core, an undercoat, an enteric coating, and a misoprostol mantle. The tablet had the following composition.

|  | Unit Formula (mg) |
|---|---|
| Core | |
| diclofenac sodium | 50.0 |
| lactose (monohydrate) | 13.0 |
| microcrystalline cellulose | 12.9 |
| cornstarch | 8.4 |

|  | Unit Formula (mg) |
| --- | --- |
| povidone K-30 | 4.8 |
| magnesium stearate | 0.9 |
| Undercoat | |
| HPMC | 1.84 |
| PEG 400 | 0.037 |
| Enteric coating (aqueous) | |
| Aquateric | 6.56 |
| polysorbate 80 | 0.13 |
| diethyl phthalate (DEP) | 1.97 |
| Mantle | |
| misoprostol:HPMC dispersion (1:100) | |
| misoprostol | 0.2 |
| hydroxypropyl methylcellulose | 20.0 |
| crospovidone | 10.0 |
| colloidal silicon dioxide | 0.5 |
| hydrogenated castor oil | 1.0 |
| microcrystalline cellulose | 233.3 |

EXAMPLE 9

A pharmaceutical tablet composition was prepared consisting of a diclofenac sodium central core, an undercoat, an enteric coating, an overcoat and a misoprostol mantle. The tablet had the following composition.

|  | Unit Formula (mg) |
| --- | --- |
| Core | |
| diclofenac sodium | 50.0 |
| lactose (monohydrate) | 13.0 |
| microcrystalline cellulose | 12.9 |
| cornstarch | 8.4 |
| povidone K-30 | 4.8 |
| magnesium stearate | 0.9 |
| Undercoat | |
| HPMC | 1.84 |
| PEG 400 | 0.037 |
| Enteric coating (aqueous) | |
| Aquateric | 6.56 |
| polysorbate 80 | 0.13 |
| diethyl phthalate (DEP) | 1.97 |
| Overcoating | |
| HMPC | 2.70 |
| PEG 400 | 0.054 |
| Mantle | |
| misoprostol:HPMC dispersion (1:100) | |
| misoprostol | 0.2 |
| hydroxypropyl methylcellulose | 20.0 |
| crospovidone | 10.0 |
| colloidal silicon dioxide | 0.5 |
| hydrogenated castor oil | 1.0 |
| microcrystalline cellulose | 233.3 |

The composition that is the invention herein provides an ease of delivery of an NSAID for its therapeutic value such as the alleviation of inflammation in a system which limits the undesirable side affects of ulcerogenesis associated with such NSAID therapy. That is, the composition herein consisting of essentially a core/mantle tablet provides a prostaglandin along with the NSAID whereby the prostaglandin can be administered for its beneficial therapeutic value in preventing and or inhibiting the incidence of NSAID induced ulcers.

A particularly beneficial aspect of the invention herein is that the combination of the two components in a core/mantle tablet assures compliance with the therapeutic regimen of the two active components. That is, a co-administration of the active components (NSAID and prostaglandin) separately can be difficult to achieve and can be difficult for a patient to faithfully follow. By placing the two active components in the same tablet or composition, adherence to the therapeutic regimen is controlled as the administration of the tablet containing the NSAID assures compliance of the administration of the prostaglandin also present in the tablet.

The composition herein is especially utile as the composition herein exhibits a stability for the prostaglandin and the NSAID.

We claim:

1. A pharmaceutical tablet composition comprising:
   a. a core consisting of a therapeutically-effective amount of a nonsteroidal anti-inflammatory agent selected from diclofenac and piroxicam; and
   b. a mantle coating surrounding the core comprising a therapeutically-effective amount of misoprostol.

2. A pharmaceutical composition as recited in claim 1 wherein the NSAID comprises diclofenac.

3. A pharmaceutical composition as recited in claim 1 wherein the NSAID comprises piroxicam.

4. A pharmaceutical composition as recited in claim 1 further comprising an intermediate enteric coating surrounding the core.

5. A pharmaceutical composition as recited in claim 1 wherein the NSAID comprises diclofenac from about 25 to 75 mg and the mantle coating comprises a prostaglandin formulation containing an amount of about 200 mcg of misoprostol.

6. A method of treating inflammation comprising orally administering to a patient in need of such treatment, a therapeutically effective amount to treat inflammation of a composition comprising
   a. a core consisting of a therapeutically-effective amount of a nonsteroidal anti-inflammatory agent selected from diclofenac and piroxicam; and
   b. a mantle coating surrounding the core comprising a therapeutically-effective amount of misoprostol.

7. A method as recited in claim 6 wherein the nonsteroidal anti-inflammatory agent comprises diclofenac.

8. A method as recited in claim 6 wherein the nonsteroidal anti-inflammatory agent comprises piroxicam.

9. A method as recited in claim 6 wherein the NSAID comprises diclofenac from about 25 to 75 mg and the mantle coating comprises a prostaglandin formulation containing an amount of about 200 mcg of misoprostol.

10. A pharmaceutical tablet composition comprising:
    a. a core comprising from about 25 to 75 mg of diclofenac sodium;
    b. an enteric coating surrounding the core; and
    c. a mantle coating surrounding the enteric coating, the mantle coating comprising from about 100 to about 200 μg misoprostol.

* * * * *